(12) United States Patent
Myers

(10) Patent No.: US 7,879,387 B2
(45) Date of Patent: Feb. 1, 2011

(54) PROCESS OF ELECTROSTATICALLY COATING A STENT ON A CATHETER

(75) Inventor: Randy Joe Myers, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 25 days.

(21) Appl. No.: 12/013,927

(22) Filed: Jan. 14, 2008

(65) Prior Publication Data

US 2008/0113084 A1    May 15, 2008

Related U.S. Application Data

(62) Division of application No. 10/738,812, filed on Dec. 16, 2003, now abandoned.

(51) Int. Cl.
*A61L 33/00* (2006.01)

(52) U.S. Cl. .................. 427/2.24; 600/381; 623/1.15; 606/194; 606/41; 606/47; 606/49; 606/21; 604/53; 427/2.25; 427/458; 427/472; 427/474; 427/475; 427/476; 427/181; 427/183; 427/230; 427/231; 427/233; 427/234; 427/239

(58) Field of Classification Search .................. 600/381; 427/2.25; 606/21, 194, 41, 47; 623/1.15; 604/103.1, 53, 96
See application file for complete search history.

(56) References Cited

U.S. PATENT DOCUMENTS

| | | | |
|---|---|---|---|
| 4,270,449 A | 6/1981 | Ito et al. .................. 101/129 |
| 4,749,125 A | 6/1988 | Escallon et al. ................ 239/3 |
| 4,930,494 A | 6/1990 | Takehana et al. ................ 128/4 |
| 5,086,973 A | 2/1992 | Escallon et al. ................ 239/3 |
| 5,165,601 A | 11/1992 | Rodenberger et al. .......... 239/3 |
| 5,305,320 A | 4/1994 | Andrews et al. ............... 604/53 |
| 5,332,154 A | 7/1994 | Maier et al. .................... 239/3 |
| 5,431,638 A | 7/1995 | Hennig et al. ............... 604/264 |
| 5,609,629 A | 3/1997 | Fearnot et al. ............. 623/1.42 |
| 5,634,476 A | 6/1997 | Orkin et al. .................. 128/775 |
| 5,681,308 A | 10/1997 | Edwards et al. ............... 606/41 |
| 5,807,306 A | 9/1998 | Shapland et al. .............. 604/21 |
| 5,938,623 A | 8/1999 | Quiachon et al. ........... 600/585 |
| 5,944,710 A | 8/1999 | Dev et al. .................... 604/500 |
| 6,032,061 A | 2/2000 | Koblish ...................... 600/372 |
| 6,091,980 A * | 7/2000 | Squire et al. ................. 600/381 |
| 6,096,070 A | 8/2000 | Ragheb et al. ............. 623/1.39 |
| 6,156,028 A | 12/2000 | Prescott ......................... 606/2 |
| 6,156,254 A | 12/2000 | Andrews et al. ............ 264/231 |
| 6,245,020 B1 | 6/2001 | Moore et al. ................ 600/466 |
| 6,256,525 B1 | 7/2001 | Yang et al. .................. 600/373 |
| 6,299,604 B1 | 10/2001 | Ragheb et al. .............. 604/265 |
| 6,308,097 B1 | 10/2001 | Pearlman .................... 600/547 |

(Continued)

OTHER PUBLICATIONS

U.S. Appl. No. 10/738,812, filed Dec. 16, 2003.

*Primary Examiner*—Michael Barr
*Assistant Examiner*—Andrew Bowman
(74) *Attorney, Agent, or Firm*—Brinks Hofer Gilson & Lione

(57) ABSTRACT

A process for electrostatically coating a stent on a catheter. A conductor which is permanently affixed to the catheter contacts a stent mounted on the catheter. Conductive ink applied to the catheter may be used as the conductor. An electrical charge is applied to the conductor. The stent is then coated using an electrostatic coating process.

17 Claims, 1 Drawing Sheet

U.S. PATENT DOCUMENTS

| | | | |
|---|---|---|---|
| 6,347,247 B1 | 2/2002 | Dev et al. | 607/2 |
| 6,355,058 B1 * | 3/2002 | Pacetti et al. | 623/1.15 |
| 6,356,779 B1 | 3/2002 | Katzenmaier et al. | 600/391 |
| 6,357,447 B1 | 3/2002 | Swanson et al. | 128/898 |
| 6,364,903 B2 | 4/2002 | Tseng et al. | 623/1.15 |
| 6,368,658 B1 | 4/2002 | Schwarz et al. | 427/2.15 |
| 6,394,949 B1 | 5/2002 | Crowley et al. | 600/127 |
| 6,409,716 B1 | 6/2002 | Sahatjian et al. | 604/509 |
| 6,416,505 B1 | 7/2002 | Fleischman et al. | 606/1 |
| 6,421,556 B2 | 7/2002 | Swanson | 600/510 |
| 6,428,537 B1 | 8/2002 | Swanson et al. | 606/41 |
| 6,440,488 B2 | 8/2002 | Griffin, III et al. | 427/2.3 |
| 6,450,965 B2 | 9/2002 | Williams et al. | 600/467 |
| 6,463,323 B1 | 10/2002 | Conrad-Vlasak et al. | 607/2 |
| 6,468,271 B1 | 10/2002 | Wentzel et al. | 606/34 |
| 6,468,272 B1 | 10/2002 | Koblish et al. | 606/41 |
| 6,500,144 B1 | 12/2002 | Russell et al. | 604/95.01 |
| 6,511,478 B1 | 1/2003 | Burnside et al. | 606/41 |
| 6,529,756 B1 | 3/2003 | Phan et al. | 600/374 |
| 6,537,310 B1 | 3/2003 | Palmaz et al. | 623/1.13 |
| 6,575,966 B2 | 6/2003 | Lane et al. | 606/21 |
| 6,579,690 B1 | 6/2003 | Bonnecaze et al. | 435/14 |
| 6,589,546 B2 | 7/2003 | Kamath et al. | 424/423 |
| 6,596,699 B2 | 7/2003 | Zamora et al. | 514/44 |
| 6,607,598 B2 | 8/2003 | Schwarz et al. | 118/500 |
| 6,610,055 B1 | 8/2003 | Swanson et al. | 606/41 |
| 6,613,046 B1 | 9/2003 | Jenkins et al. | 606/41 |
| 6,736,841 B2 | 5/2004 | Musbach et al. | 623/1.11 |
| 6,749,628 B1 | 6/2004 | Cho et al. | 623/1.15 |
| 2001/0032013 A1 | 10/2001 | Marton | 623/1.15 |
| 2002/0026236 A1 | 2/2002 | Helmus et al. | 623/1.42 |
| 2002/0045668 A1 | 4/2002 | Dang et al. | 514/649 |
| 2002/0045894 A1 * | 4/2002 | Joye et al. | 606/21 |
| 2002/0103445 A1 | 8/2002 | Rahdert et al. | 600/549 |
| 2002/0128234 A1 | 9/2002 | Hubbell et al. | 436/518 |
| 2002/0128640 A1 | 9/2002 | Swanson | 606/32 |
| 2002/0133224 A1 | 9/2002 | Bajgar et al. | 623/1.39 |
| 2002/0172829 A1 | 11/2002 | Mori et al. | 428/407 |
| 2002/0177899 A1 | 11/2002 | Eum et al. | 623/23.7 |
| 2002/0188324 A1 | 12/2002 | Blinn et al. | 607/3 |
| 2003/0003221 A1 | 1/2003 | Zhong et al. | 427/2.1 |
| 2003/0018381 A1 | 1/2003 | Whitcher et al. | 623/1.15 |
| 2003/0054090 A1 | 3/2003 | Hansen | 427/2.1 |
| 2003/0130615 A1 | 7/2003 | Tom | 604/65 |
| 2003/0158548 A1 | 8/2003 | Phan et al. | 606/41 |
| 2003/0185964 A1 * | 10/2003 | Weber et al. | 427/2.25 |
| 2003/0204238 A1 | 10/2003 | Tedeschi | 623/1.1 |

* cited by examiner

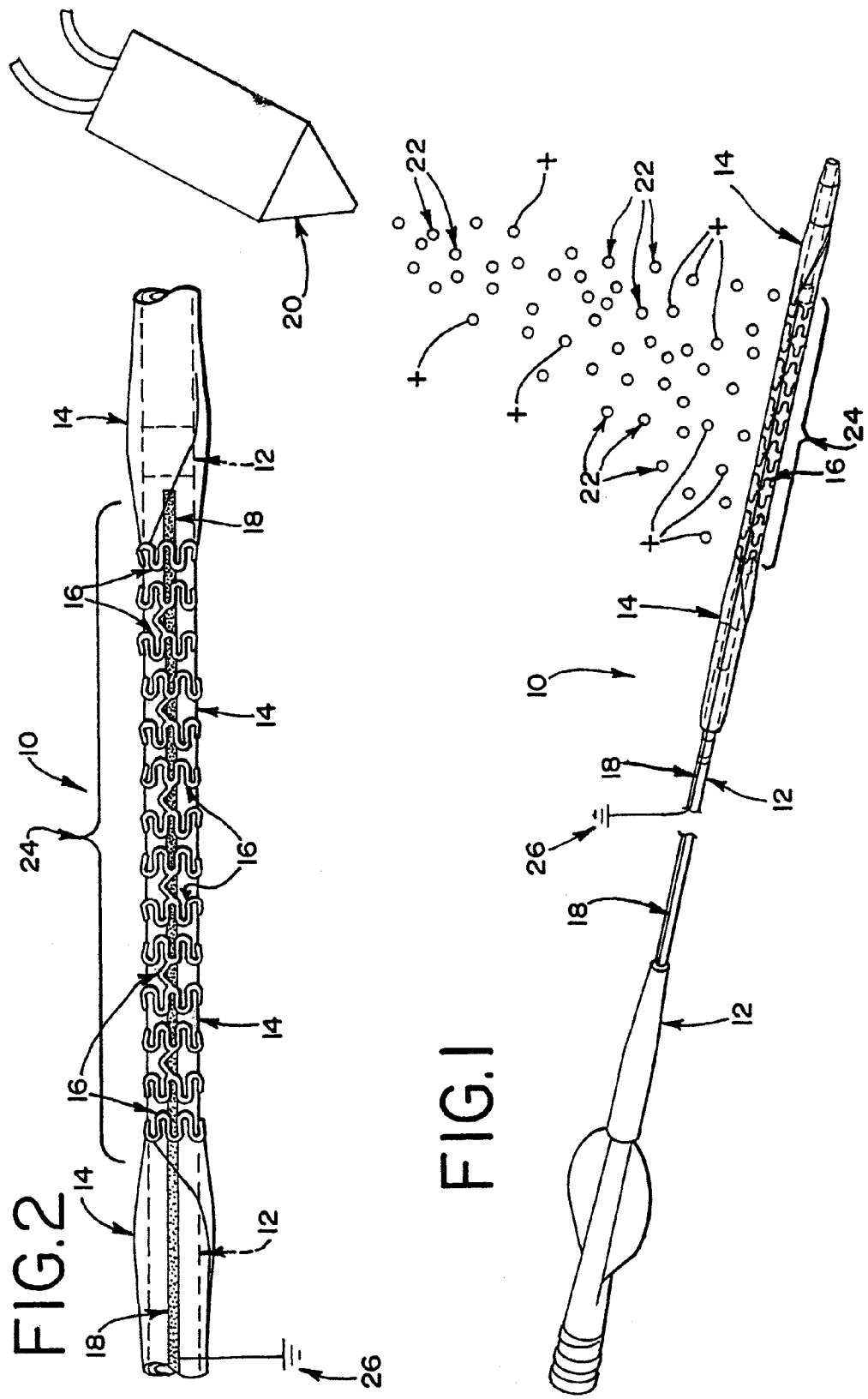

PROCESS OF ELECTROSTATICALLY COATING A STENT ON A CATHETER

This application is a divisional of U.S. patent application Ser. No. 10/738,812, filed Dec. 16, 2003, which is hereby incorporated by reference herein.

BACKGROUND

The present invention relates generally to medical devices and particularly to a catheter used to implant stents which has a permanently affixed conductor.

The use of stents to treat various organs, such as the vascular system, colon, biliary tract, urinary tract, esophagus, trachea and the like, has become common. Typically, stents are useful in treating blockages, occlusions, narrowing ailments and other similar problems that restrict flow through a passageway.

One common medical treatment in which stents are used involves implanting an endovascular stent into the vascular system. Stents are useful for numerous medical treatments of various vessels throughout the vascular system, including both coronary vessels and peripheral vessels (e.g., carotid, brachial, renal, iliac and femoral). However, the use of stents in coronary vessels has drawn particular attention from the medical community due to the commonality of heart problems caused by stenosis (i.e., narrowing of a vessel).

Although stenosis may occur for a variety of reasons, one of the most common causes of coronary stenosis results from the buildup of atherosclerotic plaques along the lumen of the vessel. The resulting coronary stenosis restricts blood flow through the vessel, which eventually can lead to a dangerously increased risk of heart attacks.

The medical community has attempted to address coronary stenosis (along with the many other passageway problems that patients suffer from) with various versions of percutaneous transluminal angioplasty ("PTA"). Fundamentally, PTA involves inserting a balloon-tipped catheter into a vessel and threading the catheter to the narrowed portion to be treated. The balloon is then expanded at the narrowed portion by pumping saline through the catheter to the balloon. As a result, the balloon expands, contacts the inner vessel wall, and forces the vessel to dilate. The balloon is then deflated and retracted from the vessel.

One problem that has been encountered with typical PTA procedures is restenosis (i.e., re-narrowing) of the vessel. Restenosis may occur for a variety of reasons, such as collapsing of the vessel wall or growth of cellular tissue. For example, restenosis may occur due to damage caused to the vessel lining during balloon expansion and vessel dilating. As a result of the damage caused to the intima layers of the vessel, the vessel attempts to grow new intima tissue to repair the damage. This tendency of vessels to regrow new tissue is referred to as neointimal hyperplasia. The effect of this response results in a re-narrowing of the vessel. However, restenosis is not completely predictable and may occur either abruptly soon after the PTA procedure due to vessel collapse or may occur slowly over a longer period of time due to other reasons.

One approach the medical community has tried in order to overcome the problems with restenosis is to use stents in conjunction with the above-described PTA procedure. Traditionally, stents are made of metal or other synthetic materials, thereby providing a tubular support structure that radially supports the inner wall of the vessel. Although other materials are possible and are sometimes used, the most common materials now used in stents are stainless steel (e.g., 316L SS and 304 SS) and Nitinol. Typically, stents are designed with a pattern of openings formed in the support structure that permits the stent to radially expand from a small diameter to a larger diameter. Accordingly, stents are now commonly used in conjunction with conventional PTA procedures by positioning the stent within the portion of the vessel that has been dilated by the balloon and radially expanding the stent against the inner wall of the vessel to permanently implant the stent. The expectation of this revised PTA procedure is that the support structure of the implanted stent will mechanically prevent the vessel from collapsing back to its original narrowed condition.

Although stent designs and implantation procedures vary widely, two categories are common.

The first of these two categories may be referred to as balloon-expandable stents. Balloon-expandable stents are generally made from ductile materials that plastically deform relatively easily. In the case of stents made from metal, 316L stainless steel that has been annealed is a common choice for this type of stent. One common procedure for implanting a balloon-expandable stent involves mounting the stent circumferentially on the balloon prior to threading the balloon-tipped catheter to the narrowed vessel portion that is to be treated. When the balloon is positioned at the narrowed vessel portion and expanded, the balloon simultaneously dilates the vessel and also radially expands the stent into the dilated portion. The balloon and the catheter are then retracted, leaving the expanded stent permanently implanted at the desired location. Ductile metal lends itself to this type of stent since the stent may be compressed by plastic deformation to a small diameter when mounted onto the balloon. When the balloon is then expanded in the vessel, the stent is once again plastically deformed to a larger diameter to provide the desired radial support structure. Traditionally, balloon-expandable stents have been more commonly used in coronary vessels than in peripheral vessels due to the deformable nature of these stents. One reason for this is that peripheral vessels tend to experience frequent traumas from external sources (e.g., impacts to a person's arms, legs, etc.) which are transmitted through the body's tissues to the vessel. In the case of peripheral vessels, there is an increased risk that an external trauma could cause a balloon-expandable stent to once again plastically deform in unexpected ways with potentially severe and/or catastrophic results. In the case of coronary vessels, however, this risk is minimal since coronary vessels rarely experience traumas transmitted from external sources.

A second common category of stents is referred to as self-expandable stents. Self-expandable stents are generally made of shape memory materials that act like a spring. Typical metals used in this type of stent include Nitinol and 304 stainless steel. A common procedure for implanting a self-expandable stent involves a two-step process. First, the narrowed vessel is dilated with the balloon as described above. Second, the stent is implanted into the dilated vessel portion. To accomplish the stent implantation, the stent is installed on the end of a catheter in a compressed, small diameter state and is retained in the small diameter by inserting the stent into the lumen of the catheter or by other means. The stent is then guided to the balloon-dilated portion and is released from the catheter and allowed to radially spring outward to an expanded diameter until the stent contacts and presses against the vessel wall. Traditionally, self-expandable stents have been more commonly used in peripheral vessels than in coronary vessels due to the shape memory characteristic of the metals used in these stents. One advantage of self-expandable stents for peripheral vessels is that traumas from external sources do not permanently deform the stent. Instead, the stent may temporarily deform during an unusually harsh trauma but will spring back to its expanded state once the trauma is relieved. Self-expandable stents, however, are often considered to be less preferred for coronary vessels as compared to balloon-expandable stents. One reason for this is that balloon-expandable stents can be precisely sized to a particular vessel diameter and shape since the ductile metal that is used can be plastically deformed to a desired size and shape. In contrast, self-expandable stents are designed with a particular expansible range. Thus, after being installed self-expandable stents continue to exert pressure against the vessel wall.

However, even when a stent is used in conjunction with conventional PTA procedures, restenosis still remains a problem. As discussed above, one cause of restenosis is neointimal hyperplasia which may result from damage to the vessel wall. This cause of neointimal hyperplasia remains a problem even when a stent is used. In addition, the synthetic materials that are usually used in stents may also contribute to neointimal hyperplasia. The cause of this problem is the body's tendency to grow new living tissues around and over newly implanted foreign objects. Thus, despite the mechanical support structure provided by the stent, restenosis remains a problem.

One approach that has been offered to address the problem of restenosis has been to coat stents with drugs that are designed to inhibit cellular growth. Although many such drugs are known, common examples of these types of drugs include Paclitaxel, Sirolimus and Everolimus. However, despite the benefits of these types of drugs, numerous problems still exist with the current methods that are used to apply these and other coatings to stents.

Typically, a stent is provided by the manufacturer as part of a pre-assembled package. For example, in the case of a balloon-expandable stent, the package may include a catheter, a balloon formed at the end of the catheter, and a drug-coated stent mounted onto the balloon. In the case of a self-expandable stent, the package may include a catheter, a mounting apparatus for retaining and releasing the stent, and a drug-coated stent mounted on the apparatus.

One method that may be used to manufacture the above-described stent assemblies involves coating the stent first in a separate step and then mounting the coated stent onto the balloon or other mounting apparatus. Common coating processes include dipping, spraying and painting the drug onto the stent. However, these methods suffer from numerous problems. One problem is the difficulty of mounting the coated stent onto the catheter without damaging the coating that has been applied. In addition, many conventional coating processes are difficult to control and apply an uneven coating on the stent. Moreover, when the stent is coated separately, it is difficult to avoid coating at least part of both the inside and outside surfaces of the stent.

Alternatively, the stent may be coated after being mounted onto the catheter. However, this method has not been perfected. As mentioned, conventional coating processes are difficult to control and apply uneven coatings. This can be an even more significant problem when the coating is applied to a stent mounted to a catheter since the coating inevitably ends up coating the catheter, balloon and/or mounting apparatus also.

Precisely controlling the application of coatings on stents is important for a number of reasons. For example, in the case of drug coatings in particular, it is important to ensure that the drug is applied as evenly as possible on the specific surfaces where the coating is needed. This ensures a uniform physiological response to the drug after the stent is implanted. Another important reason for precisely controlling the application of coatings is the high cost of many coatings. Typically, in the case of drug coatings, the cost of the drug per unit volume can be very expensive. Therefore, the drug should be applied as precisely as possible to the surfaces of the stent where the effectiveness of the drug can be maximized. Thus, by minimizing waste during the coating process, the overall cost of the stent assembly may be reduced.

It is apparent to the inventor that a stent assembly is desired in which coatings may be applied to the stent in a more effective manner than is presently possible. Accordingly, a solution is described more fully below that solves this and other problems.

SUMMARY

A stent assembly is provided with a conductor that is permanently affixed to a catheter. Preferably, the conductor is applied to the exterior of the catheter using conductive ink. The conductor extends longitudinally along the catheter and contacts the stent. One advantage of the conductor is that the stent assembly may be coated with drugs or other coatings using an electrostatic coating process. During the electrostatic coating process, the conductor is grounded or connected to an opposite electrical charge, thereby providing electrical attraction between charged coating particles and the stent. Additional details and advantages are further described below.

BRIEF DESCRIPTION OF SEVERAL VIEWS OF THE DRAWINGS

The invention may be more fully understood by reading the following description in conjunction with the drawings in which:

FIG. 1 is a side view of a catheter with a balloon and stent located at a distal end thereof, showing an electrostatic coating process; and FIG. 2 is a close-up side view of a portion of the catheter, showing the balloon and the stent with a conductor extending along a portion thereof.

DETAILED DESCRIPTION

Referring now to the figures, a stent assembly 10 is provided for use in percutaneous transluminal angioplasty ("PTA") procedures. The stent assembly 10 is provided as a pre-assembled package with the stent 16 mounted onto a balloon 14 which is formed at the end of a catheter 12. Although not shown, the principles taught herein may also be adapted to a self-expandable stent assembly in which the stent is mounted on a mounting apparatus that selectively retains and releases the stent.

The catheter 12 includes a conductor 18 that is permanently affixed to the catheter 12. As shown, the conductor 18 is affixed to the outer surface of the catheter 12 and extends longitudinally along a portion of the catheter 12. The conductor 18 may extend along the full length of the catheter 12, or the conductor 18 may extend as little as an inch or less along the catheter 12. The conductor 18 may also extend along a portion of the balloon 14. At one end, the conductor 18 contacts an inner surface of the stent 16. Since the stent 16 is metallic, an electrical connection is made between the stent 16 and the conductor 18.

In the preferred embodiment, the conductor 18 comprises conductive ink that is applied to the exterior of the catheter 12 and balloon 14 as a stripe. One type of conductive ink that may be used is a silver-based epoxy ink. Conductive ink of this type may be obtained from Creative Metals Incorporated as product number CMI 119-21 and referred to as Printable Solvent Resistant Electrically Inductive Ink. However, numerous other types of conductive ink may also be used, such as platinum-based, gold-based and copper-based inks. Non-epoxy inks may also be used, such as urethane inks. In general, any compound which may be applied in a liquid or gel form and is capable of conducting an electrical current after application may be considered conductive ink. Moreover, the conductor 18 may also comprise any other conductive material, such as conductive polymers.

The conductive ink may be applied to the catheter 12 and balloon 14 with a variety of printing processes, such as pad printing, ink jet printing, spraying, marker striping, painting or other like processes. However, pad printing is preferred since it is relatively easy with this process to apply a consistent ink stripe on the catheter 12 and balloon 14.

An advantage of the conductor 18 is that coatings 24 may be applied to the stent 16 with electrostatic coating processes instead of conventional coating processes. As shown in FIG. 1, an electrostatic spray nozzle 20 charges the coating material and dispenses charged coating particles 22 towards and around the stent 16. Examples of electrostatic coating processes that may be used are described in U.S. Pat. Nos. 4,749,125; 5,165,601; 5,086,973 and 5,332,154, which are all hereby incorporated by reference herein. Other electrostatic coating processes may also be used, and any coating process that electrically charges the coating material may be adapted for coating the stent 16. An electrical charge is also applied to the conductor 18 by either grounding the conductor 18 or by connecting the conductor 18 to a charge that is opposite to the charge of the coating particles 22. Thus, the charged coating particles 32 become electrically attracted to the stent 16. As a result, the coating particles 22 are drawn to the surfaces of the stent 16 and adhere to the stent 16 once contact is made. The coating 24 that results is considerably more consistent and uniform than coatings applied by conventional processes. The conductor 18 may be grounded 26 in any manner known to those in the art. For example, the conductor 18 may be grounded 26 by the fixture that holds the stent assembly 10 during the coating process. Collets or other known arrangements may be readily adapted to serve as a ground 26 for the conductor 18. Likewise, the conductor 18 may be connected to an opposite charge in any manner known in the art.

Electrostatic coating offers significant improvements over conventional coating processes, such as dipping, spraying and painting. One of the benefits of electrostatic coating is that the application of the coating 24 can be precisely controlled. Thus, in the case of drug coatings, a precise amount of the therapeutic agent can be applied uniformly over the stent 16 without the inconsistencies and waste of conventional processes. This is particularly helpful when typical anti-restenosis drugs are used since these drugs can be especially expensive. Other coatings 24 however may also be applied to the stent 16, such as hydrophilic coatings, with similar benefits.

There are also several advantages of coating the stent 16 after the stent 16 has been mounted to the catheter 16 as compared to separately coating the stent 16. One benefit is that damage to the coating 24 can be minimized since the manufacturer does not need to handle an already coated stent when mounting the stent 16 to the balloon 14. Another benefit is that the coating 24 is applied only to the outside surface of the stent 16 instead of being applied partially to the inside of the stent 16 as may occur when the stent 16 is coated separately. In the case of anti-restenosis drugs, this is a more efficient result since the anti-restenosis drug is primarily needed on the exterior surfaces of the stent 16 where the stent 16 contacts the vessel wall after implantation. Although the electrically charged coating particles 22 will be attracted primarily to the metallic stent 16 as compared to the non-metallic balloon, some of the drug coating 24 (or any other coating used) can be expected to pass through the openings in the stent 16 and adhere to the balloon 14 instead of the stent 16. However, even these balloon-coated portions may provide some benefits since these coated portions may contact the vessel wall during balloon expansion, thereby being transferred to the vessel wall.

A further advantage of the conductor 18 is that it is permanently affixed to the catheter 12. One alternative approach that could be used to electrostatically coat a stent 16 involves positioning a loose ground wire under or adjacent the stent 16 to make an electrical connection. However, this approach is undesirable because the loose wire may be inadvertently left attached to the stent assembly 10 after coating. This could have serious consequences if the loose wire is not removed prior to a surgeon using the stent assembly 10 in a PTA procedure. In addition, even when the wire is properly removed during manufacturing of the stent assembly 10, the removal step could damage the stent assembly 10. One possible risk is that the wire might puncture the balloon 14. In addition, removal of the wire may dislodge some of the coating 24.

The conductor may also provide other advantages as well. For example, the conductor 18 may improve visualization of the catheter 12 and stent assembly 10 during implantation by showing up more distinctly in imaging devices. Moreover, if the conductor 18 is extended along the entire longitudinal length of the catheter 12, the conductor 18 could be used during PTA or other surgical procedures to supply electrical current to the internal area of the body that is being treated.

It is now apparent that there are many advantages of the invention provided herein. In addition to the many advantages that have been described, it is possible that there are other advantages of the invention that are not currently recognized but which may become apparent at a later time.

While a preferred embodiment of the invention has been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. A method of coating a stent, comprising:
   permanently affixing a conductor to a catheter, said conductor extending along a longitudinal portion of said catheter;
   mounting a metallic stent on said catheter, wherein said metallic stent contacts said conductor;
   electrically charging a coating material and dispensing said charged coating material in proximity to said metallic stent; and
   applying an electrical charge to said conductor, wherein said charged coating material is attracted to said metallic stent, whereby an exterior surface of said metallic stent is electrostatically coated with said coating material.

2. The method according to claim 1, wherein said conductor comprises conductive ink applied to said catheter, and said conductor is disposed on an outer surface of said catheter.

3. The method according to claim 2, wherein a balloon is located at a distal end of said catheter, said stent being mounted on said balloon, and said conductor extends along a portion of said balloon.

4. The method according to claim 3, wherein said conductive ink is applied by pad printing, and said conductor contacts an inner surface of said stent.

5. The method according to claim 1, wherein said conductor is one of silver-based, platinum-based, gold-based and copper-based.

6. The method according to claim 1, wherein said coating material is a drug.

7. The method according to claim 1, wherein at least a portion of said coating material is applied to said conductor.

8. The method according to claim 1, wherein at least a portion of said coating material is applied to said catheter.

9. The method according to claim 1, wherein at least a portion of an inner surface of said stent is not coated by said coating material.

10. The method according to claim 1, wherein at least a portion of said coating material is applied to said catheter and at least a portion of an inner surface of said stent is not coated by said coating material.

11. The method according to claim 10, wherein a balloon is located at a distal end of said catheter, said stent being mounted on said balloon, and said conductor extends along a portion of said balloon.

12. The method according to claim 11, wherein at least a portion of said coating material is applied to said conductor.

13. The method according to claim 12, wherein said conductor comprises conductive ink applied to said catheter, and said conductor is disposed on an outer surface of said balloon.

14. The method according to claim 13, wherein said conductive ink is applied by pad printing, and said conductor contacts an inner surface of said stent and said conductor is one of silver-based, platinum-based, gold-based and copper-based.

15. The method according to claim 1, wherein said conductor comprises conductive ink applied to said catheter, and said conductor is disposed on an outer surface of said catheter, wherein a balloon is located at a distal end of said catheter, said stent being mounted on said balloon, and said conductor extends along a portion of said balloon, wherein at least a portion of said coating material is applied to said conductor and at least a portion of an inner surface of said stent is not coated by said coating material.

16. A method of coating a stent, comprising:
permanently affixing a conductor to a balloon located at a distal end of a catheter, said conductor comprising conductive ink applied to an outer surface of said balloon and extending along a portion of said balloon;
mounting a metallic stent on said balloon, wherein an inner surface of said metallic stent contacts said conductor;
electrically charging a coating material and dispensing said charged coating material in proximity to said metallic stent; and
applying an electrical charge to said conductor, wherein said charged coating material is attracted to said metallic stent, whereby an exterior surface of said metallic stent is electrostatically coated with said coating material;
wherein at least a portion of said coating material is applied to said balloon and at least a portion of said inner surface of said stent is not coated by said coating material.

17. The method according to claim 16, wherein said conductive ink is applied by pad printing and said conductor is one of silver-based, platinum-based, gold-based and copper-based, wherein said coating material is a drug and at least a portion of said coating material is applied to said conductor.

* * * * *